(12) United States Patent
Blanquet Grossard et al.

(10) Patent No.: US 7,001,767 B2
(45) Date of Patent: Feb. 21, 2006

(54) METHOD FOR IN VITRO PROPAGATION OF THE AGENT RESPONSIBLE FOR TRANSMISSIBLE SPONGIFORM ENCEPHALOPATHIES

(75) Inventors: Francoise Blanquet Grossard, St Etienne de St Geoire (FR); Jean-Yves Cesbron, Meylan (FR); Catherine Lemaire Vieille, St Martin D'uriage (FR); Jerome Follet, Lille (FR)

(73) Assignee: Universite Joseph Fourier (Grenoble 1), Grenoble (FR)

( * ) Notice: Subject to any disclaimer, the term of this patent is extended or adjusted under 35 U.S.C. 154(b) by 0 days.

(21) Appl. No.: 10/380,800

(22) PCT Filed: Sep. 20, 2001

(86) PCT No.: PCT/FR01/02933

§ 371 (c)(1),
(2), (4) Date: May 12, 2003

(87) PCT Pub. No.: WO02/24871

PCT Pub. Date: Mar. 28, 2002

(65) Prior Publication Data

US 2003/0170816 A1    Sep. 11, 2003

(30) Foreign Application Priority Data

Sep. 20, 2000    (FR) .................................. 00 11989

(51) Int. Cl.
*C12N 5/00*    (2006.01)
(52) U.S. Cl. ..................... 435/325; 424/93.7; 435/363; 435/366
(58) Field of Classification Search ............... 424/93.7; 435/325, 363, 366; 800/3, 13, 18
See application file for complete search history.

(56) References Cited

OTHER PUBLICATIONS

M. Moser et al., "Developmental Expression of the Prion Protein Gene in Glial Cells," *Neuron*, vol. 14, No. 3, pp. 509-517, Mar. 1995.
V. M. Roikhel et al., "Persistence of the Scrapie Agent in Glial Cells fro Rat Gasserian Ganglion," *Acta Virologica*, vol. 31, No. 1, pp. 36-42, 1987.
P. Markovits et al., "Effects of *In Vitro* Infection of Mouse Glial and Neuroblastoma Cells with Scrapie Agent," *Annales De Recherches Veterinaires*, vol. 16, No. 1, pp. 111-119, 1985.
Butler et al., "Scrapie-Infected Murine Neuroblastoma Cells Produce Protease-Resistant Prion Proteins", Journal of Virology, May 1988, pp 1558-1564.
Schatzl et al., "A Hypothalamic Neuronal Cell Line Persistently Infected with Scrapie Prions Exhibits Apoptosis", Journal of Virology, Nov. 1997, pp. 8821-8831.
Fischer et al., "Prion protein (PrP) with amino-proximal deletions restoring susceptibility of PrP knockout mice to scrapie", The EMBO Journal, vol. 15 No. 6, pp 1255-1264, 1996.
Lemaire-Vieille et al., "Epithelial and endothelial expression of the green fluorescent protein gene under the control of bovine prion protein (PrP) gene regulatory sequences in transgenic mice", PNAS, May 9, 2000, vol. 97, No. 10, pp 5422-5427.
Brandner et al., "Normal host prion protein necessary for scrapie-induced neurotoxicity", NATURE, VOL. 379, Jan. 25, 1996, pp 339-343.

*Primary Examiner*—Ulrike Winkler
(74) *Attorney, Agent, or Firm*—Oliff & Berridge, PLC

(57) ABSTRACT

The invention concerns a method for in vitro propagation of the agent responsible for transmissible spongiform encephalopathies, or prion, comprising steps which consist in: providing a culture or a glial cell line and in infecting the culture or line with the agent responsible for transmissible spongiform encephalopathies or prion. Said method enables to obtain infected cell line capable of being used to assess the efficacy of a molecule in the reduction or inhibition of the infectiosity of the prion or for detecting the prion.

5 Claims, No Drawings

METHOD FOR IN VITRO PROPAGATION OF THE AGENT RESPONSIBLE FOR TRANSMISSIBLE SPONGIFORM ENCEPHALOPATHIES

The invention relates to a method for in vitro propagation of the agent responsible for transmissible spongiform encephalopathies (TSEs), or prion, making it possible to conserve the infecting capacity of the prion.

TSEs include mainly scrapie, bovine spongiform encephalopathy, Creutzfeldt-Jakob disease and Kuru in humans.

These neurodegenerative diseases are characterized by thy appearance of an abnormal form of the $PrP^c$ protein naturally present at the surface of certain cells, and in particular of neurones.

The $PrP^c$ protein, or prion protein, is a cell surface sialoglycoprotein which plays a primordial role in transmissible spongiform encephalopathies in humans and animals. In these diseases, $PrP^c$ is converted to a pathogenic form called $PrP^{sc}$, which is thought to be an abnormal isoform of $PrP^c$, which has been shown to be essential to infectivity and which is today considered to be the infectious agent of these diseases.

The process of transformation of $PrP^c$ to $PrP^{sc}$ remains undetermined and few tools are currently available for studying the mechanism of action of this infectious agent, in particular for the purpose of detecting it and searching for therapeutic treatments to treat the diseases which it causes.

According to the publication by C. Lemaire-Vieille et al., PNAS, vol. 97, No. 10 of May 9, 2000*, Epithelial and endothelial expression of the green fluorescent protein reporter gene under the control of bovine prion protein* (*PrP*) *gene regulatory sequences in transgenic mice*, the authors of the studies obtained several transgenic mouse lines which express the reporter gene of a fluorescent protein (gfp), under the control of regulatory sequences of the bovine PrP protein gene. Exposure to UV radiation of histological sections derived from organs taken from these mice makes it possible to locate the production of fluorescence and therefore to identify the cells capable of expressing the PrP gene. The authors thus observed that the sites of production were cerebellar Purkinje cells, lymphocytes, epithelial cells of the medullar region of the thymus, keratinocytes and endothelial cells of the blood capillaries of the intestinal villi.

These studies have therefore made it possible to have a study model from which it is then possible to determine the sites of expression of the prion gene.

The authors of the present invention have discovered that the glial cells of the nervous system, and in particular the glial cells of the peripheral nervous system and the Schwann cells, constitute a suitable site for the in vitro propagation of the prion.

To date, only very few cell lines are known which are capable of perpetuating the infectious capacity of the agent responsible for TSEs; these are the N2a cell line derived from mouse neuroblastoma cells [Butler, J. Virol. (1988) 62, 1558–1564], the PC12 cell line derived from rat pheochromocytoma cells [Rubenstein, J. Gen. Virol. (1984) 65, 2191–2198], the GT1 cell line derived from neuronal cells from the hypothalamus [Schatz, J. Virol. (1997) 11, 8821–8831] and the 1C11 cell line derived from neuroectoderm cells [Mouillet-Richard, Microbes Infect. (1999) 12, 969–976].

In the article V. M. Roikhel et al., Acta Virologica, vol. 31, No. 1 (1987) 36–42, the authors demonstrated that cells derived from the rat Gasser's node, NGUK-I cells, could be infected in vitro and conserve their infectious capacity. The NGUK-I cells were characterized and have a growth profile which is that of astrocytes and a morphological profile which is that of epithelial cells (A. P. Avtsyn et al., Tsitologiia (January 1989) 1, 97–102).

None of the cells previously mentioned are glial cells and the discovery according to the present invention is surprising in that glial cells are not neuronal cells and that the infectivity which develops therein, as is shown below, is strong.

Thus, a first object of the invention is a method for in vitro propagation of the prion, according to which a glial cell culture or a glial cell line is provided and the culture or the line is infected with the agent responsible for TSEs, or prion. More particularly, said agent is of murine origin. Advantageously, the glial cells are glial cells of the peripheral nervous system or Schwann cells.

Before describing the invention in greater detail, some terms used in the description and the claims are defined below.

According to the invention, the expression "propagation of the prion in a cell culture" is understood to mean that, after infection, or infestation, of at least one cell of the starting cell culture or of the starting cell line, the infectious capacity of the prion is conserved in the derived cells, i.e. the cells resulting from subcultures.

The prion used to infect the starting culture or line is chosen from prion strains such as the Chandler strain or the RML (Rocky Mountain Laboratory) strain, or from the cells of a primary culture, i.e. cells taken directly from an infected tissue. By way of example, they may be brain tissues taken post-mortem from mice.

Preferential variants of the method above and of other subjects of the invention are now presented.

The method is advantageously carried out using a culture or a line of Schwann cells of murine origin; a preferred line is the MSC-80 line.

The invention also relates to a line of glial cells infected with the prion, capable of propagating the prion; the cells of the line are advantageously derived from Schwann cells, and more particularly derived from cells of the murine Schwann cell line MSC-80, after infection with the prion.

Another subject of the invention is a method of evaluating the effectiveness of a molecule, of an agent or of a composition in decreasing or inhibiting the infectiousness of the prion, according to which method a culture of glial cells or of glial cells of the peripheral nervous system infected with the prion or a cell line of the invention, or an extract thereof, is brought into contact with said molecule, said agent or said composition, at predetermined doses, and the decrease in or the inhibition of the infectiousness of the prion is detected. The detection step can be carried out in Tga 20 mice.

The invention also provides a method for detecting and, optionally, quantifying the prion, in a biological sample, according to which said sample is brought into contact with a culture or a line of glial cells or of glial cells of the peripheral nervous system, under conditions which allow the infection thereof, and the infection or noninfection of said line with said sample is detected. The glial cells are preferably Schwann cells, and in particular the glial cell line is the MSC-80 line.

Yet another subject of the invention is the use of the MSC-80 cell line for propagating the prion in vitro.

The present invention is illustrated below with the following examples.

EXAMPLE 1

Infection of the MSC-80 Line and Demonstration of this Infection

MSC-80 murine Schwann cells are cultured in six-well dishes ($2 \times 10^5$ cells per well), for 48 hours before infection, in a culture medium consisting of Dulbecco's modified Eagle medium (DMEM) supplemented with 10% of fetal calf serum (Life Technologies, Paisley, UK), L-glutamine at a final concentration of 2 mM (Life Technologies) and 100 U/ml of penicillin/100 µg of streptomycin (SEROMED).

A 10% (weight/volume) homogenate of mouse brains infected with the RML (Rocky Mountain Laboratory) prion strain is obtained by mechanical grinding in the culture medium described above, followed by passing through 16-gauge and then 22-gauge needles, and heated to 80° C. for 20 minutes.

The MSC-80 cells are then brought into contact with 1 ml per well of homogenate diluted to 2%, at 37° C. for 72 hours. The inoculum and the medium thus used are renewed every 24 hours. After 72 hours, the culture medium supernatant is replaced with 2 ml of fresh culture medium. The cells are cultured until confluence. The content of each well is then distributed into 75 cm², then 150 cm², culture flasks and is split at ¹/₁₀ in 150 cm² flasks every 7 days.

The presence of the $PrP^{sc}$ protein is detected by Western blotting. The cells ($8 \times 10^6$) are lysed in 200 µl of buffer (Triton-DOC) for 15 minutes on ice. The amount of proteins in the supernatant is assayed and adjusted to 1 mg/ml with lysis buffer.

One milligram of total proteins is then digested with 20 µg of proteinase K (BOEHRINGER MANNHEIM, Meylan, France) at 37° C. for 30 minutes, so as to destroy the (normal) $PrP^c$ proteins. The reaction is stopped for 5 minutes on ice, after the addition of phenylmethylsulfonyl fluoride (SIGMA, St Louis, Mo.) at a final concentration of 2 mM. The digestion product is centrifuged for 45 minutes at 14 000 g. The pellet is taken up in 20 µl of Laemmli buffer, heated at 100° C. for 5 minutes, and loaded onto a 12% polyacrylamide gel.

After migration in a Tris-glycine buffer at 50 mA for 2 hours, the gel is electrotransferred onto a nitrocellulose membrane for 2 hours. The $PrP^{sc}$ protein is then detected using a mixture of an equivalent amount of three monoclonal antibodies (SAF60, SAF69 and SAF70; GRASSI, CEA Saclay, France). The presence of these antibodies is revealed with an anti-mouse immunoglobulin antibody coupled to peroxidase, which will enable revelation by chemiluminescence (ECL kit, AMERSHAM LIFE SCIENCE, Little Chalfont, UK).

EXAMPLE 2

Demonstration of the Propagation of the Prion

The infectious capacity of the prion propagated according to example 1 was analyzed by intracerebral inoculation of Tga20 mice, available at the Zurich Institut de Neuropathologie [Institute of Neuropathology] (S. Brander et al., Nature (1996) 379, 339–343; M. Fisher et al., EMBO J., (1996) 15, 1255–1264).

A first batch of Tga20 mice was inoculated with the Chandler prion strain, a second batch of mice was inoculated with $MSC^{Ct}$ control murine Schwann cells, and a third batch of mice was inoculated with $MSC^{Ch}$ infected Schwann cells, described in example 1.

This third batch was obtained by inoculating the mice with extracts of infected cells of example 1, resulting from the seventh passage.

At the final stage of the disease, the $PrP^{sc}$ is identified by Western blotting after partial digestion with proteinase K (cf. example 1). The profile obtained in the extracts of brains from the mice inoculated with the $MSC^{Ch}$ cells is identical to that obtained in the mice inoculated with the Chandler strain.

Immunohistochemical analysis with antibodies directed against the glial fibrillary acidic protein (GFAP) reveals, in the tegument of the mesencephalon of the mice inoculated with the $MSC^{Ch}$ cells, astrocytic hypertrophy and hyperplasia. These brains also exhibit neuropil vacuolization visible after hematoxilin-eosin staining.

88 days after inoculation, the abovementioned infected mice exhibit hyperactivation and loss of balance. They die after 91.5±5 days.

The same observations were observed when replacing this third batch with a fourth batch obtained by inoculation of the mice with extracts of infected cells of example 1, resulting from the twenty-second passage.

What is claimed is:

1. An isolated line of Schwann cells infected with a prion, capable of propagating the prion, wherein said Schwann cells are of the peripheral nervous system.

2. The isolated line as claimed in claim 1, characterized in that the cells are derived from cells of the murine Schwann cell line MSC-80, after infection with the prion.

3. A method of evaluating the effectiveness of a composition for decreasing or inhibiting the infectious prion protein, wherein the method comprises contacting the cell line as claimed in claim 1 with said composition, at predetermined doses, and measuring the infectious prion protein, a detected decrease in infectious prion protein in the cell line indicating an effective composition.

4. The method as claimed in claim 3, characterized in that the decrease in or the inhibition of the infectious prion protein is detected in Tga20 mice.

5. The method as claimed in claim 3, wherein the cells are derived from cells of the murine Schwann cell line MSC-80, after infection with a prion.

* * * * *